United States Patent [19]

Vincent et al.

[11] Patent Number: 4,725,581

[45] Date of Patent: Feb. 16, 1988

[54] NEW PEPTIDE COMPOUNDS HAVING A LACTONE OR CYCLOAMIDE STRUCTURE

[75] Inventors: Michel Vincent, Bagneux; Georges Remond, Versailles; Jean Lepagnol, Chatou, all of France

[73] Assignee: ADIR et Compagnie, Neuilly-sur-Seine, France

[21] Appl. No.: 892,345

[22] Filed: Aug. 1, 1986

[30] Foreign Application Priority Data

Aug. 5, 1985 [FR] France ............................ 85 11936

[51] Int. Cl.[4] .................... A61K 37/02; C07K 5/08; C07K 5/02
[52] U.S. Cl. .................................... 514/18; 514/19; 530/332; 530/331
[58] Field of Search ................. 530/331, 332; 514/18, 514/19

[56] References Cited

U.S. PATENT DOCUMENTS

| 4,100,152 | 7/1978 | Fujino et al. | 530/331 |
| 4,260,601 | 4/1981 | Reichelt et al. | 530/331 |
| 4,504,470 | 3/1985 | Uda et al. | 530/331 |

*Primary Examiner*—Delbert R. Phillips
*Attorney, Agent, or Firm*—Gordon W. Hueschen

[57] ABSTRACT

New peptide compounds having a lactone or cycloamide structure and containing a saturated bicyclic structure, pharmaceutically-acceptable acid addition salts thereof, method for the preparation thereof, pharmaceutical compositions containing the same, and use thereof for the stimulation of cyclic AMP in the cerebral tissue and consequently increasing the metabolic capacities of the brain, thereby making them of interest in the treatment of diseases of the central nervous system or disorders approximating normal or pathological aging, are disclosed.

13 Claims, No Drawings

NEW PEPTIDE COMPOUNDS HAVING A LACTONE OR CYCLOAMIDE STRUCTURE

The present invention relates to new peptide compounds having a lactone or cycloamide structure, a process for the preparation thereof and pharmaceutical compositions containing them.

Some endogenous tripeptides having a cycloamide structure are known, in particular TRH (pyroglutamyl-histidyl-prolinamide) which has endocrine system effects (stimulation of the secretion of TSH and prolactin), and behavioural effects on the central nervous system, occurring through a stimulation of the liberation of acetyl-choline in the hippocampus (motor, or memorising stimulations).

However, TRH is metabolically rapidly rendered inactive in the organism in 2 to 5 minutes.

Other peptides have been described (FR Pat. Nos. 2,187,155 and 2,287,916, 2,266,515, 2,345,448) in which the pyroglutamyl radical is replaced by another heterocyclic carboxylic acid radical, especially 2-oxotetrahydrofuran-5-carboxylic acid, 1,2,5,6-tetrahydro-2,6-dioxo-pyrimidine-4-carboxylic acid or 2-oxo-piperidine-6-carboxylic acid. These compounds have an anti-convulsant and anti-depressant activity.

The compounds of the present invention in which the prolinamide radical is replaced by a saturated bicyclic structure have the very interesting properties of stimulating the synthesis of cyclic AMP in the cerebral tissue and thus of increasing the metabolic capacities of the brain and of improving the capacities of central neurotransmission whether cholinergic or catecholaminergic, whilst at the same time exhibiting resistance to tissular or plasmatic enzymes.

The invention relates more especially to new compounds having a lactone or cycloamide structure corresponding to the general formula I

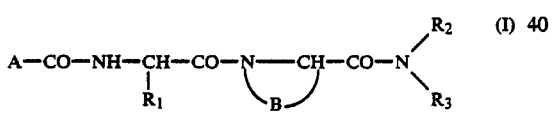

in which:

A represents a 2-oxo-5-tetrahydrofuryl, 2-oxo-5-pyrrolidinyl or 2-oxo-6-piperidinyl group optionally substituted at the nitrogen atom by a straight-chain or branched alkyl group having from 1 to 4 carbon atoms, or represents a 2,6-dioxo-1,2,3,6-tetrahydro-4-pyrimidinyl group, B represents, together with the carbon and nitrogen atom to which it is attached, a saturated polycyclic structure selected from the group comprising perhydroindole, perhydroisoindole, perhydroquinoline, perhydroisoquinoline, cyclopenta[b]pyrrole and 2-azabicyclo[2,2,2]octane, $R_1$ represents a hydrogen atom, a straight-chain or branched alkyl radical having from 1 to 4 carbon atoms, or an (imidazol-4-yl)methyl group optionally substituted at one of the nitrogen atoms by a straight-chain or branched alkyl radical having from 1 to 4 carbon atoms or by a benzyloxycarbonyl, 2,4-dinitrophenyl, fluorenomethoxycarbonyl, tosyl or benzyl radical, $R_2$ and $R_3$, which may be the same or different, each represents a hydrogen atom or an alkyl radical having from 1 to 4 carbon atoms, or, in conjunction with the nitrogen atom to which they are attached, together form a 1-pyrrolidinyl, 1-piperidinyl, 4-morpholinyl or 4-($C_{1-4}$-alkyl)-1-piperazinyl radical, the enantiomers and diastereoisomers thereof, and also, when $R_1$ represents an (imidazol-4-yl)methyl group optionally substituted by an alkyl radical, or when $R_2$ and $R_3$ represent an N-alkyl-1-piperazinyl radical, the addition salts thereof with a pharmaceutically acceptable acid.

Among the pharmaceutically acceptable acids there may be mentioned, by way of non-limiting example, hydrochloric, sulphuric, tartaric, maleic, fumaric, oxalic, methanesulphonic and camphoric acids etc.

The invention relates also to a process for the preparation of the compounds of the formula I, characterised in that the amine function of an amino acid of the formula II

in which B together with the nitrogen and carbon atoms to which it is attached has the same meaning as in formula I, is protected by a tert.-butoxycarbonyl (tBoc) radical by the action of di-tert.-butyl carbonate, to form a compound of the formula III

in which B has the same meaning as in formula I, which is then converted, at a temperature of between 0° and −15° C., by the successive action of ethyl chloroformate and an amine of the formula IV

in which $R_2$ and $R_3$ have the same meanings as in formula I, into an amide of the formula V:

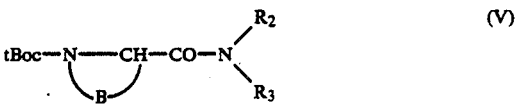

in which B, $R_2$ and $R_3$ have the same meanings as in formula I, which is de-protected by the action of gaseous hydrochloric acid in ethyl acetate, or of trifluoroacetic acid, to form a compound of the formula VI

in which B, $R_2$ and $R_3$ have the same meanings as in formula I, which is coupled with a protected amino acid of the formula VII

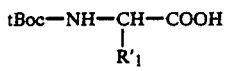

in which R′₁ represents a hydrogen atom, a straight-chain or branched alkyl radical having from 1 to 4 carbon atoms, an (N-alkyl(C₁₋₄)imidazol-4-yl)methyl radical, or an (imidazol-4-yl)methyl radical temporarily protected at one of the nitrogen atoms by a group such as a 2,4-dinitrophenyl, benzyloxycarbonyl, fluorenomethoxycarbonyl, tosyl or benzyl radical, to form a compound of the formula VIII,

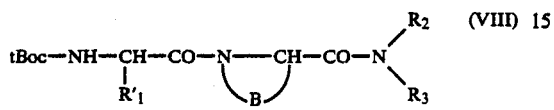

in which R′₁, R₂, R₃ and B have the same meanings as specified hereinbefore, which is de-protected as hereinbefore described to form a compound of the formula IX

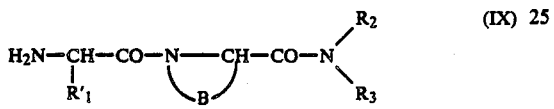

in which R′₁, R₂, R₃ and B have the same meanings as hereinbefore, which is condensed with a compound of the formula X,

in which A has the same meaning as in formula I
* either, to form a compound of the formula I′

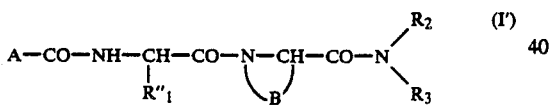

in which A, B, R₂ and R₃ have the same meanings as hereinbefore and R″₁ represents a hydrogen atom, a straight-chain or branched alkyl radical having from 1 to 4 carbon atoms or an (N-alkyl(C₁₋₄)imidazol-4-yl)methyl radical,
which compound is, if desired, directly converted into its addition salt with a pharmaceutically acceptable acid when R″₁ represents an (N-alkyl imidazolyl)methyl radical or when R₂ and R₃ represent, together with the nitrogen atom to which they are attached, a 1-piperazinyl radical substituted by an alkyl chain having from 1 to 4 carbon atoms,
or, is separated first into its enantiomers of diastereoisomers, then converted, if desired, when R″₁, R₂ and R₃ have the same meanings as those defined above, into its addition salt with a pharmaceutically acceptable acid
* or to form a compound of the formula I″

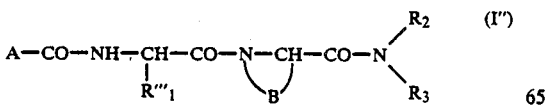

in which A, B, R₂ and R₃ have the same meanings as hereinbefore, and R‴₁ represents an (imidazol-4-yl)methyl group protected at one of the nitrogen atoms by a benzyloxycarbonyl, 2,4-dinitrophenyl, fluorenomethoxycarbonyl, tosyl or benzyl grouping,
which compound is de-protected to form a compound of the formula I‴

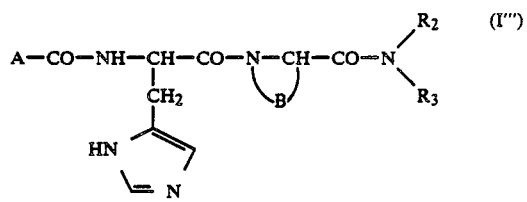

in which A, B, R₂ and R₃ have the meanings defined above,
which is, if desired, converted into its addition salt with a pharmaceutically acceptable acid, or separated into its isomers then, if necessary, formed into a salt by a pharmaceutically acceptable acid.

The totality of compounds of the formulae I′, I″ and I‴ represents the compounds of the formula I.

The compounds of the formula I have valuable pharmacological properties for animals; they increase the intracerebral content of AMPc and inhibit narcosis induced by pentobarbital. This inhibition of narcosis is reflected in particular in an effect on the uptake of choline.

Moreover, the compounds of the formula I have stimulating properties towards the routes of catecholaminergic neurotransmission because they increase the toxicity of yohimbine in mice, the hypertensive peak from noradrenalin in amyeled rats and the spontaneous locomotion and the exploring activity in mice.

The reduction in the level of AMPc with age and the reduced efficiency of cholinergic and catecholaminergic neurotransmission are associated in humans with aging amnesia disorders and senile dementias.

The compounds of the invention are thus useful therapeutically in the treatment of central nervous system disorders, (for example disorders of consciousness, of language, coma, autism, syndrome of hyperkinesia, schizophrenia, depression, Parkinson's disease . . . ) and in the treatment of disorders close to normal or pathological ageing (senile dementia, Alzheimer's disease) since they correct the metabolic disorders while stimulating the neurotransmission and restoring, for example, the AMPc rate.

The present invention relates also to pharmaceutical compositions containing as active ingredient at least one compound of the general formula I or one of the addition salts thereof with a pharmaceutically acceptable acid, on its own or in combination with one or more inert, non-toxic excipients or vehicles.

Among the pharmaceutical compositions according to the invention there may be mentioned those which are suitable for parenteral, oral or rectal administration, especially injectable or drinkable preparations, tablets, gelatin-coated pills, capsules, dragées, sachets, suppositories . . .

The posology varies according to the age and weight of the patient, the route of administration and the nature of the disorder, and may range between 1 and 200 mg per dose, which may be taken from 2 to 5 times per day.

The following Examples illustrate the invention and do not limit it in any way.

The starting materials are known from the literature or may be prepared in a similar manner.

The melting points indicated are measured according to the micro-Kofler technique. The proton nuclear magnetic resonance spectra were recorded at 60 MHz using $D_2O$ as solvent and TMS as internal reference. When the solvent is not $D_2O$, its nature is specified in the text.

EXAMPLE 1

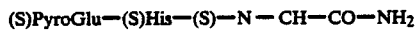
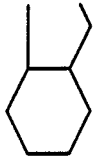

For convenience the group (2S,3aS,7aS)-2 carbonyl-perhydroindole will be designated (S)PHI Stage A: tBoc(S)PHI—OH or (2S,3aS,7aS)-1-(tert.-butoxycarbonyl)-2-perhydroindolecarboxylic acid 0.03 mol of (S)PHI—OH, obtained according to Tetrahedron Letters 23 (16) 1677–1680 (1982) is dissolved in a mixture of 60 ml of dioxan and 30 ml of water, the solution is cooled to 0° C., 70 ml of N soda is added, then, drop by drop, a solution of 0.03 mol of di-tert.-butyl carbonate in 150 ml of dioxan.

The whole is stirred for 30 mins. at a temperature of between 0° C. and 5° C., then for 2 hours at room temperature. The solvents are evaporated under reduced pressure. The residue is taken up in water rendered acidic with citric acid to a pH of 4 and the aqueous phase is extracted with ethyl acetate. The organic phase is washed with a 10% strength aqueous solution of sodium chloride, dried over anhydrous calcium sulphate, filtered and concentrated under reduced pressure. The residue is crystallised in n-pentane, filtered with suction and dried.

tBoc(S)PHI—OH is obtained, m.p.=134°
Yield=82.5%.

IR spectral characteristics $\nu OH = 2400$–$3200$ cm$^{-1}$
$\nu CO(acid) = 1750$ cm$^{-1}$
$\nu CO(-N-CO-) = 1630$ cm$^{-1}$ Stage B: (S)tBoc(S)PHI—NH$_2$ 2.10 ml (0.022 mol) of freshly distilled ethyl chloroformate are added to a solution of 5.4 g (0.02 mol) of (S)tBoc(S)PHI—OH in 25 ml of tetrahydrofuran cooled in a salted ice-bath (temperature=−10° C.). A precipitate forms and the whole is stirred for a further ¼ hour at −10° C., then 3.84 ml (0.057 mol) of concentrated ammonia are added at the same temperature and the whole is stirred again for 30 minutes, then returned to room temperature. The solvents are evaporated under reduced pressure. The residue is taken up in an aqueous solution of citric acid of pH 4 and the acidic aqueous phase is extracted with ethyl acetate. The organic phase is washed with an aqueous solution of sodium bicarbonate, then with water, dried over anhydrous calcium sulphate, filtered and concentrated under reduced pressure. The residue is crystallised in n-pentane, filtered with suction and dried.

tBoc(S)PHI—NH$_2$ is obtained.
M.p.=163° C.
Yield=75.4%.

Elemental analysis

|  | C % | H % | N % |
|---|---|---|---|
| Calculated | 62.66 | 9.01 | 10.43 |
| Found | 62.87 | 9.02 | 10.53 |

IR spectral characteristics $\nu NH_2$ amide = 3300 to 3520 cm$^{-1}$
$\nu CO$ carbonate and amide I = 1680 cm$^{-1}$
$\nu CO$ amide II = 1570 cm$^{-1}$ Stage C: (S)PHI—NH$_2$ A solution of 3 g (0.0111 mol) of (S)tBocPHI—NH$_2$ in 150 ml of anhydrous ethyl acetate is saturated with hydrogen chloride gas, left at room temperature for 12 hours, filtered with suction, washed with ethyl acetate and dried.

(S)PHI—NH$_2$,HCl is obtained in a yield of 98%.

Elemental analysis

|  | C % | H % | N % | Cl % |
|---|---|---|---|---|
| Calculated | 52.8 | 8.37 | 13.68 | 17.31 |
| Found | 53.12 | 8.50 | 13.89 | 17.20 |

IR spectral characteristics $\nu NH_2 +$ (amide) = 2200 to 3300 cm$^{-1}$,
$\nu CO$ amide (I) = 1685 cm$^{-1}$,
$\nu CO$ amide (II) = 1580–1630 cm$^{-1}$.

Stage D: tBoc(S)(2,4DNP)His—(S)PHI—NH$_2$

Using the liquid-phase peptide coupling method (DCC/HOBT) of W. KONIG and R. GEIGER (Ber. 103, 788 (1970) and dimethyl formamide as solvent, tBoc(S)(2,4DNP)His—(S)PHI—NH$_2$ is obtained in a yield of 85% from 0.0128 mol of (S)PHI—NH$_2$ obtained in the preceding stage, and from 0.0128 mol of tBoc (S)(2,4-dinitrophenyl)histidine or tBoc(S)(2,4DNP)—His.

The product is purified by chromatography on a silica column using as eluant methylene chloride/methanol (95/5). 2 g of a product of which the analyses are in conformity are obtained.

IR spectral characteristics $\nu NH,NH_2$: several bands from 3100 to 3320 cm$^{-1}$
$\nu CO$ amide I, amide II, C=N: several bands from 1540 to 1710 cm$^{-1}$.

Stage E: (S)(2,4DNP)His—(S)PHI—NH$_2$,HCl

The compound obtained in the preceding stage is de-protected by the hydrogen chloride-ethyl acetate method described in Stage C. From 3.5 g (0.00647 mol) of tBoc(S)(2,4DNP)His—(S)PHI—NH$_2$, 3.4 g of the hydrochloride of (S)(2,4DNP)His—(S)PHI—NH$_2$ are obtained.

IR spectral characteristics $\nu NH,NH_2+$: 3580—2200 cm$^{-1}$,
$\nu CO$ amide (I): 1690 cm$^{-1}$,
$\nu CO$ amide (II): 1540 cm$^{-1}$,
$\nu CO$ tertiary amide: 1640 cm$^{-1}$.

Stage F: (S)PyroGlu—(S)(2,4DNP)His—(S)PHI—NH$_2$

Using the liquid-phase peptide coupling method (DCC/HOBT) described in Stage D, there is obtained from 0.0055 mol of (S)pyroglutamic acid or (S)Pyro- Glu—OH and from 0.0055 mol of (S)(2,4DNP)His—(S)PHI—NH₂ obtained in the preceding stage, after customary treatment, a crude product which is chromatographed on silica using as eluant a mixture of methylene chloride and methanol (85/15) and 1 g of the desired product is recovered in a yield of 31.2%.

NMR spectral characteristics (CDCl₃)

0.8 to 2.5 ppm: 15H (CH and CH₂),
2.5 to 5 ppm: 6H CH ($\alpha$ with respect to CO and CN, CH₂ $\alpha$ with respect to imidazole),
6.7 and 7.5 to 8.5 ppm: 4H exchangeable (NH and NH₂),
7.3-8.1 ppm: 2H(CH imidazole),
7.9-8.7 and 8.9 ppm: 3H aromatic.

Stage G: (S)PyroGlu—(S)His—(S)PHI—NH2

By applying the method of de-protection described by R. F. NUTT, F. W. HOLLY et al. J. Med. Chem. 24, 692–698 (1981) to 1 g (0.0017 mol) of the tripeptide obtained in the preceding stage, dissolved in 10 ml of anhydrous dimethylformamide and stirred under a nitrogen atmosphere with 1 ml (0.014 mol) of 2-mercaptoethanol for 14 hours, there is obtained, after evaporation of the solvents under reduced pressure, a yellow residue which is chromatographed on a column of silica using as eluant a mixture of acetone and water (90/10).

The pure product obtained is taken up in water, filtered over a micron filter and lyophilised. 325 mg of (S)PyroGlu—(S)His—(S)PHI—NH₂ (yield 46.5%) are obtained.

Elemental analysis: corrected for water

|  | C % | H % | N % |
|---|---|---|---|
| Calculated | 57.67 | 6.77 | 20.17 |
| Found | 57.46 | 6.46 | 20.02 |

Thin layer chromatography shows a single spot product in the system acetone/water (80/20), which can be developed by the PAULY reagent.

EXAMPLE 2

(S)Blc—(S)His—(S)PHI—NH₂

By replacing the (S)PyroGlu—OH in stage F of Example 1 with (S) Y-butyrolactonecarboxylic acid (or 2-oxotetrahydrofuran-5-carboxylic acid) or (S)Blc-OH (prepared according to O. LERVINKA and L. HUB Coll. Czech. Chem. Comm., 33, 2927 (1968)), there are obtained in succession, in the same manner:
Stage F: (S)Blc—(S)(2,4—DNP)His—(S)PHI—NH₂ (yield: 65%)
Stage G: (S)Blc—(S)His—(S)PHI—NH₂(Yield: 29%) which is lyophilised.

IR spectral characteristics $\nu$NH, NH₂, OH(H₂O)=2500 to 3600 cm⁻¹,
$\nu$CO lactone: 1780 cm⁻¹,
$\nu$CO amide (I) and (II)=1630-1680 and 1530 cm⁻¹.

Elemental analysis corrected for water (% of H₂O=4.20)

|  | C % | H % | N % |
|---|---|---|---|
| Calculated | 57.54 | 6.51 | 16.77 |
| Found | 57.63 | 6.27 | 16.79 |

EXAMPLE 3

(S)HomoPyroGlu—(S)His—(S)PHI—NH₂

By replacing (S)PyroGlu—OH in stage F of Example 1 with homopyroglutamic acid (2-oxopiperidine-6-carboxylic acid) or (S)HomoPyroGlu—OH (prepared according to J. P. GREENSTEIN, S. M. BIRNBAUM J.A.C.S. 75 1994 (1953) there are obtained in succession, in the same manner:
Stage F: (S)HomoPyroGlu—(S)(2,4DNP)His—(S)PHI—NH₂ (quantitative yield)
Stage G: (S)HomoPyroGlu—(S)His—(S)PHI—NH₂ (yield 14.4%) which is lyophilised.

Spectral characteristics

IR:
$\nu$NH,NH₂,OH(H₂O)=3000 to 3600 cm⁻¹.
$\nu$CO (lactam, primary amide, amide (I) wide band 1620-1680 cm⁻¹.
$\nu$CO (amide (II)) 1550 cm⁻¹.
NMR:
1 to 2.6 ppm: 17H (broad signal) (CH₂ and CH),
3 ppm: 2H (CH₂ at $\alpha$ with respect to imidazole),
3.9 to 5 ppm: 4H (CH $\alpha$ with respect to CO and C—N),
7 to 7.7 ppm: 2H (imidazole).

EXAMPLE 4

Orotyl—(S)His—(S)PHI—NH₂

By replacing the (S)PyroGlu—OH in Stage F of Example 1 with orotic acid (commercial product) the following are obtained in succession in the same manner:
Stage F: Orotyl—(S)(2,4DNP)His—(S)PHI—NH₂ (yield=96.2%),
Stage G: Orotyl—(S)His—(S)PHI—NH₂ (yield=13%) which is lyophilised.

Spectral characteristics

IR:
$\nu$NH₂, NH 2400 to 3600 cm⁻¹
$\nu$CO amide(I), amide(II)uracil: 1550 to 1730 cm⁻¹
NMR:
1 to 2.3 ppm: 11H(CH₂ and CH),
3.1 ppm: 2H(CH₂ $\alpha$ with respect to imidazole),
4 to 5 ppm: 3H (CH $\alpha$ with respect to CO and C—N),
6.1 ppm: 1H (CH of orotyl),
7.2 to 8.2 ppm: 2H (imidazole).

EXAMPLE 5

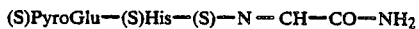

The radical (S)3-carbonyl-2-azabicyclo[2,2,2]octane will hereinafter be designated (S)ABO.

By replacing (S)PHI—NH₂ in Stage D of Example 1 with (S)ABO—NH₂ (prepared as in stages A, B, C from (S)ABO—OH described in European Pat. No. 51020)

the following compounds are obtained in the same manner:
Stage D tBoc(2,4DNP)His—(S)ABO—NH$_2$ (yield=84%),
Stage E (S)(2,4DNP)His—(S)ABO—NH$_2$, HCl (yield=80%),
Stage F (S)PyroGlu—(S)(2,4DNP)His—(S)ABO—NH$_2$ (yield=69%),
Stage G (S)PyroGlu—(S)His—(S)ABO—NH$_2$ (yield: 24%),
which is converted into its hydrochloride by lyophilisation in the presence of the stoichiometric amount of 0.1N hydrochloric acid.

Elemental analysis (corrected for 2.9% H$_2$O)

|  | C % | H % | N % | Cl % |
|---|---|---|---|---|
| Calculated | 51.99 | 6.20 | 19.14 | 8.07 |
| Found | 51.91 | 6.50 | 18.60 | 8.05 |

Spectral characteristics

IR:
$\nu$NH, NH$_2$NH$^+$, OH(H$_2$O) 2300 to 3600 cm$^{-1}$,
$\nu$CO amide (I) and lactam 1530 and 1570 cm$^{-1}$,
$\nu$CO amide (II) 1530 cm$^{-1}$.
NMR:
1.5 to 2.6 ppm: 13H (CH$_2$, CH),
3.2 ppm: 2H (CH$_2$ $\alpha$ with respect to imidazole),
4 to 5.5 ppm: 4H (CH $\alpha$ with respect to CO and C—N),
7.4 and 8.7 ppm: 2H (imidazole).

EXAMPLE 6

Orotyl—(S)His—(S)ABO—NH$_2$

By replacing (S)pyroglutamic acid in Stage F of Example 5 with orotic acid, there are obtained in succession in the same manner:
Stage F: Orotyl(S)(2,4DNP)His—(S)ABO—NH$_2$ (yield: 43%)
Stage G: Orotyl(S)His—(S)ABO—NH$_2$ (yield: 57%) which is converted into its hydrochloride by lyophilisation with the stoichiometric amount of 0.1N HCl.

NMR spectral characteristics 1.4 to 2.4 ppm: 9H (CH and CH$_2$)
3.3 ppm: 2H (CH$_2$ $\alpha$ with respect to imidazole)
3.8 to 5.5 ppm: 4H (CH $\alpha$ with respect to CO and C—N)
6.2 ppm: 1H (orotyl)
7.4 to 8.7 ppm: 2H (imidazole)
Thin layer chromatography shows a single spot product, (acetone/water (90/10)) which can be developed with PAULY reagent.

EXAMPLE 7

(S)HomoPyroGlu—(S)His—(S)ABO—NH$_2$

By replacing (S)pyroglutamic acid in Stage F of Example 5 with (S)homopyroglutamic acid there are obtained in succession in the same manner:
Stage F: (S)HomoPyroGlu—(S)(2,4DNP)His—(S)ABO—NH$_2$ (yield: 15%),
Stage G: (S)HomoPyroGlu—(S)His—(S)ABO—NH$_2$ (yield: 53%), the product is lyophilised.

Elemental analysis (corrected for 4.9% water)

|  | C % | H % | N % |
|---|---|---|---|
| Calculated | 57.68 | 6.77 | 20.77 |
| Found | 57.74 | 6.52 | 19.65 |

Spectral characteristics

IR:
$\nu$NH, OH(H$_2$O)=2600 to 3700 cm$^{-1}$
$\nu$CO (lactam-amide I, II, primary, tertiary amide): 1600 to 1700 cm$^{-1}$
NMR:
1.3 to 2.5 ppm: 15H (CH$_2$CH),
3 ppm: 2H (CH$_2$ $\alpha$ with respect to imidazole),
3.8 to 5.3: 4H ($\alpha$ with respect to CO and C—N),
7.1 to 7.7 ppm: 2H (imidazole).

EXAMPLE 8

(S)PyroGlu(S)NVa—(S)PHI—NH$_2$

By replacing tBoc(S)(2,4DNP)His in Stage D of Example 1 with tBoc(S)norvaline or tBoc(S)NVa, there are obtained in succession in the same manner:
Stage D: tBoc(S)NVa—(S)PHI—NH$_2$ (yield 89.7%),
Stage E: (S)NVa—(S)PHI—NH$_2$ (quantitative yield),
Stage F: (S)(Z)PyroGlu—(S)NVa—(S)PHI—NH$_2$, (yield: 54%),
Stage G: (S)PyroGlu—(S)NVa—(S)PHI—NH$_2$.
The (S)PyroGlu group is de-protected by catalytic hydrogenation in ethanol in the presence of palladium-on-carbon. After filtration of the catalyst, and evaporation of the solvent under reduced pressure the colourless resin obtained is taken up in distilled water, filtered and lyophilised to yield the desired product in a quantitative yield.

Elemental analysis (corrected for 4.6% water)

|  | C % | H % | N % |
|---|---|---|---|
| Calculated | 60.29 | 7.98 | 14.80 |
| Found | 60.01 | 7.67 | 14.76 |

Spectral characteristics

IR:
$\nu$NH,H$_2$O: 3700 to 3100 cm$^{-1}$,
$\nu$CO amide (I): 1680–1630 cm$^{-1}$,
$\nu$amide II=1550 cm$^{-1}$,
$\nu$CO amide (II): 1550 cm$^{-1}$.

NMR: (CDCl$_3$)

0.9 ppm: 3H(CH$_3$),
1–2.5 ppm: 16H (CH$_2$,CH), 2H(NCO—CH$_2$),
4.1 ppm: 1H (CH $\alpha$ with respect to CO—N),
4.5 ppm: 3H (CH $\alpha$ with respect to CO, CN),
5.4 ppm: 1H exchangeable,
7 ppm: 3H exchangeable,
$[\alpha]_D^{21.5}$=73.2° (value corrected for 2.7% water, titrated simultaneously).

EXAMPLE 9

(S)PyroGlu-(S)(1-methylHis)—(S)PHI—NH$_2$

By replacing the tBoc(2,4DNP)His in Stage D of Example 1 with tBoc(1-methylHis), the following are obtained in succession in the same manner:

Stage D: (S)tBoc(1-methylHis)—(S)PHI—NH$_2$ (Yield: 83%)
Stage E: (S)(1-methylHis)(S)PHI—NH$_2$ (Quantitative yield)
Stage F: (S)PyroGlu—(S)(1-methylHis)—(S)PHI—NH$_2$ (Yield 30%)

IR spectral characteristics $\nu$NH: 3600 to 3100 cm$^{-1}$,
$\nu$CO (lactam): 1685 cm$^{-1}$,
$\nu$amide I: 1630 cm$^{-1}$,
$\nu$amide II: 1545 cm$^{-1}$.

EXAMPLE 10

(S)PyroGlu—(S)(3-methylHis)—(S)PHI—NH$_2$

By replacing the tBoc(1-methylHis) in the preceding Example with tBoc(3-methylHis) the following are obtained in the same manner:
Stage D: (S)tBoc(3-methylHis)—(S)PHI—NH$_2$ (Yield; 80%),
Stage E: (S)(3-methylHis)—(S)PHI—NH$_2$ (Quantitative yield),
Stage F: (S)PyroGlu—(S)(3-methylHis)—(S)PHI—NH$_2$ (Yield: 30%), Elemental analysis (corrected for 3.2% water)

|  | C % | H % | N % |
|---|---|---|---|
| Calculated | 58.58 | 7.08 | 19.52 |
| Found | 58.82 | 6.93 | 18.49 |

IR spectral characteristics $\nu$NH, OH(H$_2$O): 3700 to 3000 cm$^{-1}$,
$\nu$CO (lactam): 1690 cm$^{-1}$,
$\nu$amide I: 1640 cm$^{-1}$,
$\nu$amide II: 1550 cm$^{-1}$.

EXAMPLE 11

(S)PyroGlu—(S)His—(S)PHI—MePip

By replacing the ammonia in Stage B of Example 1 with a stoichiometric amount of 4-methylpiperazine, or MePip—H, the following are obtained in succession in the same manner:
Stage B: tBoc—(S)PHI—MePip (Yield: 48%),
Stage C: (S)PHI—MePip (Yield: 90%),
Stage D: tBoc—(S)(2,4DNP)His—(S)PHI—MePip (Yield: 84%),
Stage E: (S)(2,4DNP)His—(S)PHI—MePip (Quantitative yield),
Stage F: (S)PyroGlu—(S)(2,4DNP)His—(S)PHI—MePip (Yield: 32%),
Stage G: (S)PyroGlu—(S)His—(S)PHI—MePip (Yield: 47%).

Elemental analysis (corrected for 6.3% water)

|  | C % | H % | N % |
|---|---|---|---|
| Calculated | 60.10 | 7.46 | 19.62 |
| Found | 59.23 | 6.96 | 19.24 |

Spectral characteristics

IR
$\nu$OH(H$_2$O): 3700 cm$^{-1}$,
$\nu$NH: 3500 to 2400 cm$^{-1}$,
$\nu$CO (lactam): 1700 cm$^{-1}$,
$\nu$CO (amide): 1680 to 1600 cm$^{-1}$.

NMR (CDCl$_3$)

1-5 ppm: 32H (CH, CH$_2$, CH$_3$): broad signal,
6.85 ppm: 1H (singlet, imidazole: CH $\alpha$ with respect to the carbon chain),
7.52 ppm: 1H (singlet, imidazole: CH $\alpha$ with respect to the two nitrogen atoms),
7.5–8.2 ppm: 3H (NH, exchangeable).

EXAMPLE 12

(S)PyroGlu—(S)Leu(S)—PHI—Mor

By replacing the ammonia in Stage B of Example 1 with a calculated quantity of morpholine (Mor—H) and replacing the tBoc(S)(2,4DNP)His in Stage D of Example 1 with tBoc(S)leucine or tBoc(S)Leu, the following are obtained in succession:
Stage B: tBoc(S)PHI—Mor (Yield: 81%),
Stage C: (S)PHI—Mor (Quantitative yield),
Stage D: tBoc(S)—Leu—(S)PHI—Mor (Yield 80%),
Stage E: (S)—Leu—(S)—PHI—Mor (Quantitative yield),
Stage F: (S)PyroGlu—(S)Leu—(S)PHI—Mor (Yield: 35%).

Elemental analysis (corrected for 3.5% water)

|  | C % | H % | N % |
|---|---|---|---|
| Calculated | 62.31 | 8.28 | 12.11 |
| Found | 61.95 | 7.80 | 11.95 |

Spectral characteristics

IR
$\nu$(C=O) (lactam): 1700 cm$^{-1}$,
$\nu$(C=O) (amide): 1650 to 1620 cm$^{-1}$.

NMR (CDCl$_3$)

0.9 ppm: 6H doublet (2CH$_3$),
1 to 3 ppm: 18H broad signal (CH, CH$_2$),
3 to 4.2 ppm: 9H broad signal (CH, CH$_2$) (morpholine-1H from PHI, $\alpha$ with respect to the nitrogen atom),
4.0 to 5.5 ppm: 3H broad signal CH ($\alpha$ with respect to the C=O).
7.4 to 8.0 ppm: 2H broad signal: NH exchangeable.

EXAMPLE 13

(S)PyroGlu—(S)NVa—(S)PHI—N(C$_2$H$_5$)$_2$

By replacing the ammonia in Stage B of Example 1 with a calculated quantity of diethylamine and the tBoc(S)(2,4DNP)His in Stage B of Example 1 with tBoc(S)norvaline or tBoc(S)NVa there are obtained in succession in the same manner:
Stage B: tBoc(S)PHI—N(C$_2$H$_5$)$_2$ (Yield 96%),
Stage C: (S)PHI—N(C$_2$H$_5$)$_2$ (Quantitative yield),
Stage D: tBoc(S)—NVa—(S)PHI—N(C$_2$H$_5$)$_2$ (Yield: 62%),
Stage E: (S)NVa—(S)PHI—N(C$_2$H$_5$)$_2$ (Quantitative yield),
Stage G: (S)PyroGlu—(S)NVa—(S)PHI—N(C$_2$H$_5$)$_2$ (Yield: 42%).

Elemental analysis (corrected for 1.8% water)

|  | C % | H % | N % |
|---|---|---|---|
| Calculated | 63.56 | 8.81 | 12.89 |
| Found | 63.75 | 8.63 | 12.78 |

Spectral characterstics

IR
$\nu$NH and OH(H$_2$O): 3700 to 2300 cm$^{-1}$,
$\nu$C=O (lactam and amide): 1700 to 1600 cm$^{-1}$,
$\nu$C=O (amide II): 1540 cm$^{-1}$.

NMR (CDCl$_3$, +D$_2$O)

0.9 ppm: 3H (CH$_3$, NVal),
1.2 ppm: 6H (2CH$_3$, 2CH$_2$—CH$_3$),
1.6 ppm: 16H (CH$_2$),
2.3 ppm: 3H (CH$_2$α with respect to the CO, pyrrolidone CHβ with respect to the nitrogen atom, PHI),
3.4 ppm: 4H (2CH$_2$, 2CH$_2$—CH$_3$),
4.1 ppm: 1H (CH, α with respect to the nitrogen atom, PHI),
4.7 ppm: 3H (CH, α with respect to the CO),
7.4 ppm: 2H (NH exchangeable).

EXAMPLE 14

(S)PyroGlu—(S)Leu—(S)PHIQ—NH$_2$

By replacing the (S)PHI—OH in Stage A of example 1 with (S)perhydroisoquinoline-3-carboxylic acid or (S)PHIQ—OH and the tBoc(2,4DNP)His in Stage D of Example 1 with tBocLeu, there are obtained in succession:
Stage A: tBoc—(S)PHIQ—OH (Yield: 81%),
Stage B: tBoc—(S)PHIQ—NH$_2$ (Yield: 73%),
Stage C: (S)PHIQ—NH$_2$ (Quantitative yield),
Stage D: tBoc(S)Leu—(S)PHIQ—NH$_2$ (Yield: 82%),
Stage E: (S)Leu—(S)PHIQ—NH$_2$ (Quantitative yield),
Stage F: (S)PyroGlu—(S)—Leu—(S)PHIQ—NH$_2$ (Yield: 44%).

IR spectral characteristics $\nu$(NH): 3600 to 3100 cm$^{-1}$,
$\nu$(C=O) (lactam): 1700 cm$^{-1}$,
$\nu$CO (amide I): 1650 to 1620 cm$^{-1}$,
$\nu$CO (amide II): 1550 cm$^{-1}$.

EXAMPLE 15

(S)BLC—(S)His—(S)ABO—NH$_2$

By replacing the pyroglutamic acid in Stage F of Example 5 with (S)γbutyrolactone carboxylic acid, the following are obtained in the same manner:
Stage F: (S)BLC—(S)(2,4DNP)His—(S)—ABO—NH$_2$ (Yield: 70%),
Stage G: (S)BLC—(S)His—(S)ABO—NH$_2$ (Yield: 41%).

NMR spectral characteristics (D$_2$O)

1.4–2.8 ppm: 13H (broad signal) (CHCH$_2$),
3.0 ppm: 2H (doublet) (CH$_2$ α with respect to imidazole),
3.7–5.3 ppm: 4H (broad signal) (CH, α with respect to CO and CN),
7–7.8 ppm: 2H (imidazole).

PHARMACOLOGICAL STUDY

EXAMPLE 16

Stimulation of the synthesis of cerebral AMPc

The compounds to be tested are administered intraperitoneally at a dose of 10 mg/kg to mice of strain OF$_1$/IFFA-Credo.

Five minutes after injection, the animals are sacrificed by freezing and the AMPc present in the cerebral structures is measured by radio immunology according to the Amersham method (specific binding protein).

Whereas the TRH used as a reference increases the intracerebral content of AMPc by 46%, the compounds according to the invention induce a twofold increase (for example +95% and +102%, respectively, for the compounds of Examples 1 and 2).

EXAMPLE 17

Increase in the latency of the onset of sleep induced by Pentobarbital

Pentobarbital, injected in rats at a dose of 40 mg/kg i.p., induces the onset of sleep. The compounds of the invention, administered at a dose of 10 mg/kg i.p. before the injection of pentobarbital, delays the onset of sleep (+110% with the compound of Example 2), thus proving an inhibition of the uptake of acetyl-choline. Under the same conditions TRH is inactive.

EXAMPLE 18

Potentialisation of the toxicity of Yohimbine

Yohimbine, injected to mice at a dose of 35 mg/kg i.p. causes the death of 10% to 30% treated animals. The compounds of the invention administered at a dose of 10 mg/kg i.p. 15 minutes before the injection of Yohimbine increase the rate of mortality (+80% with compounds of examples 5 and 7). In same conditions, a similar activity is noted with T.R.H.

EXAMPLE 19

Increase of spontaneous motility

The compounds of the invention are administered intraperitoneally at a dose of 30 mg/kg to mice divided into groups of three placed on an automatic recorder after one hour of spontaneous exploration. During the following hour, the spontaneous motility is compared to that of non treated mice. The compounds of the invention increase the spontaneous motility. The compound of example 5 is active as early as the tenth minute after treatment and the effect is identical 60 minutes after.

EXAMPLE OF GALENICAL FORMULATION

EXAMPLE 20

Tablets each containing 25 mg of (S)PyroGlu—(S)His—(S)PHI—NH$_2$

| (S)PyroGlu-(S)His-(S)PHI—NH$_2$ | 25 mg |
|---|---|
| lactose | 50 mg |
| talc | 5 mg |
| corn starch | 50 mg |
| polyvinylpyrrolidone | 5 mg |

For one complete tablet of 135 mg.
We claim:
1. Compounds of the general formula I

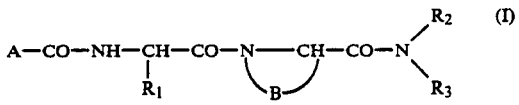

in which:
- A represents a 2-oxo-5-tetrahydrofuryl, 2-oxo-5-pyrrolidinyl or 2-oxo-6-piperidinyl grouping optionally substituted at the nitrogen atom by a straight-chain or branched alkyl grouping having from 1 to 4 carbon atoms, or represents a 2,6-dioxo-1,2,3,6-tetrahydro-4-pyrimidinyl grouping,
- B represents, together with the carbon and nitrogen atom to which it is attached, a saturated polycyclic structure selected from the group comprising perhydroindole, perhydroisoindole, perhydroquinoline, pethydroisoquinoline, cyclopenta[b]pyrrole and 2-azabicyclo[2,2,2]octane,
- $R_1$ represents a hydrogen atom, a straight-chain or branched alkyl radical having from 1 to 4 carbon atoms, or an (imidazol-4-yl)methyl group optionally substituted at one of the nitrogen atoms by a straight-chain or branched alkyl radical having from 1 to 4 carbon atoms or by a benzyloxycarbonyl, 2,4-dinitrophenyl, fluorenomethoxycarbonyl, tosyl or benzyl radical,
- $R_2$ and $R_3$, which may be the same or different, each represents a hydrogen atom or an alkyl radical having from 1 to 4 carbon atoms, or, in conjunction with the nitrogen atom to which they are attached, together form a 1-pyrrolidinyl, 1-piperidinyl, 4-morpholinyl or 4-($C_{1-4}$-alkyl)-1-piperazinyl radical, the enantiomers and diastereoisomers thereof,
and also, when $R_1$ represents an (imidazol-4-yl)methyl group optionally substituted by an alkyl radical, or when $R_2$ and $R_3$ represent an N-alkyl-1-piperazinyl radical, the addition salts thereof with a pharmaceutically acceptable acid.

2. Compounds of claim 1 of the general formula I in which B together with the nitrogen and carbon atoms to which it is attached represents a perhydroindole, perhydroisoquinoline or 2-azabicyclo[2,2,2]octane structure, the enantiomers and diastereoisomers thereof, and also, when $R_1$ represents an optionally substituted (imidazol-4-yl)methyl group, or when $R_2$ and $R_3$ represent an N-alkyl-1-piperazinyl radical, the addition salts thereof with a pharmaceutically acceptable acid.

3. Compound of claim 1 of the general formula I in which B together with the nitrogen and carbon atoms to which it is attached represents a perhydroindole structure, the enantiomers and diastereoisomers thereof and also, when $R_1$ represents an optionally substituted (imidazol-4-yl)methyl group, or when $R_2$ and $R_3$ represent an N-alkyl-1-piperazinyl radical, the additions salts thereof with a pharmaceutically acceptable acid.

4. Compound of claim 1 of the general formula I in which B together with the nitrogen and carbon atoms to which it is attached represents a 2-azabicyclo[2,2,2]octane structure, the enantiomers and diastereoisomers thereof, and also, when $R_1$ represents an optionally substituted (imidazol-4-yl)methyl group, or when $R_2$ and $R_3$ represent an N-alkyl-1-piperazinyl radical, the addition salts thereof with a pharmaceutically acceptable acid.

5. Compound of claim 1 being PyroGlu—His—PHI—$NH_2$, the enantiomers or diastereoisomers thereof, as well as the addition salts thereof with a pharmaceutically acceptable acid.

6. Compound of claim 1 being Blc—His—PHI—$NH_2$, the enantiomers or diastereoisomers thereof, as well as the addition salts thereof with a pharmaceutically acceptable acid.

7. Compound of claim 1 being PyroGlu—Nva—PHI—$NH_2$, the enantiomers or diastereoisomers thereof.

8. Compound of claim 1 being PyroGlu—His—ABO—$NH_2$, the enantiomers or diastereoisomers thereof, as well as the addition salts thereof with a pharmaceutically acceptable acid.

9. Compound of claim 1 being HomopyroGlu—His—ABO—$NH_2$, the enantiomers or diastereoisomers thereof, as well as the addition salts thereof with a pharmaceutically acceptable acid.

10. Compound of claim 1 being Blc—His—ABO—$NH_2$, the enantiomers or diastereoisomers thereof, as well as the addition salts thereof with a pharmaceutically acceptable acid.

11. Pharmaceutical composition containing as active ingredient at least one compound according to any one of claim 1, on its own or together with one or more pharmaceutically acceptable inert, non-toxic excipients or vehicles.

12. Pharmaceutical composition according to claim 11 for use in stimulating the synthesis of cyclic AMP in the cerebral tissue and consequently in the treatment of disorders of senescence associated with normal or pathological aging and diseases of central nervous system.

13. A method for stimulating the synthesis of cyclic AMP in the cerebral tissue and therefore for treating a living animal body afflicted with a disease of central nervous system or with disorder close to normal or pathological aging comprising the step of administering to the said living animal an amount of a compound of claim 1 which is suitable for the alleviation of the said condition.

* * * * *

UNITED STATES PATENT AND TRADEMARK OFFICE
CERTIFICATE OF CORRECTION

PATENT NO. : 4,725,581
DATED : February 16, 1988
INVENTOR(S) : Michel Vincent, Georges Remond and Jean Lepagnol It is certified that error appears in the above—identified patent and that said Letters Patent is hereby corrected as shown below:

Col. 1, line 15; after "motor," insert -- warning, --
Col. 4, line 47; "ageing" should read -- aging --
Col. 6, line 31; "NH2" should read -- $NH_2$ --
Col. 6, line 32; "$cm^{=1}$" should read -- $cm^{-1}$ --
Col. 6, line 37; "(1970)" should read -- (1970)) --
Col. 6, line 61; "NH2" should read -- $NH_2$ --
Col. 7, line 48; "Y-butyrolactonecarboxylic" should read -- γ-butyrolactonecarboxylic"
Col. 13, line 10; "characterstics" should read -- characteristics --
Col. 15, line 18; "pethydroisoquinoline," should read -- perhydroisoquinoline, --

Signed and Sealed this

Sixth Day of September, 1988

Attest:

DONALD J. QUIGG

Attesting Officer      Commissioner of Patents and Trademarks